United States Patent [19]

Ikeda et al.

[11] Patent Number: 5,955,371

[45] Date of Patent: *Sep. 21, 1999

[54] APPARATUS FOR INHIBITING GLYCOLYSIS IN BLOOD SAMPLES

[75] Inventors: Tatsuhiko Ikeda, Kawasaki, Japan; Ajit N. Dastane, North Arlington, N.J.; Robert Losada, New York, N.Y.

[73] Assignee: Becton Dickinson and Company, Franklin Lakes, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/969,628

[22] Filed: Nov. 13, 1997

Related U.S. Application Data

[63] Continuation of application No. 08/643,388, May 6, 1996, abandoned, which is a continuation of application No. 08/287,575, Aug. 9, 1994, abandoned.

[51] Int. Cl.$^6$ .............................. B01L 3/14; G01N 33/50
[52] U.S. Cl. .................. 436/18; 252/182.29; 252/380; 422/41; 422/61; 422/102; 435/232; 435/288.1; 435/307.1; 436/176; 604/403; 604/416
[58] Field of Search .................. 422/61, 41, 102; 436/8, 17, 18, 176, 810, 826, 67, 87; 435/2, 296, 299, 232, 288.1, 307.1; 252/380, 182.29; 604/403, 416

[56] References Cited

U.S. PATENT DOCUMENTS 5,326,535   7/1994   Vogler et al. .

FOREIGN PATENT DOCUMENTS 0 202 543   11/1986   European Pat. Off. ....... G01N 33/66

*Primary Examiner*—David Saunders
*Attorney, Agent, or Firm*—Nanette S. Thomas, Esq.

[57] ABSTRACT

A blood collection device comprising formed additive particles. The additive particles are an improvement over available additive formulations that are powder blended in that the components of the additive particles of the present invention are in each formed particle. The formed additive particles comprise a fluoride salt and an ethylenediaminetetraacetate salt or a heparin salt to consistently minimize glycolysis and coagulation of a blood specimen with low hemolysis.

18 Claims, 1 Drawing Sheet

APPARATUS FOR INHIBITING GLYCOLYSIS IN BLOOD SAMPLES

CROSS-REFERENCE TO RELATED APPLICATIONS

This is a continuation of application Ser. No. 08/643,388, filed on May 6, 1996 and now abandoned, which is a continuation of application Ser. No. 08/287,575, filed on Aug. 9, 1994 and now abandoned.

BACKGROUND OF THE INVENTION

1. Field of the Invention

This invention relates to a blood collection device for use in chemistry studies. More particularly, the present invention pertains to a blood collection device comprising an additive particle formulation, which formulation has combined antiglycolysis and anticoagulation properties.

2. Description of the Related Art

In carrying out blood collection, centrifuging and measurement of the blood sugar value for a specimen, a series of steps are required. Since the steps required are time consuming due to the increased complexity of the collection and testing work efficiency tends to be poor.

When blood is allowed to remain in a tube after being collected, the blood sugar value of the specimen declines with the passage of time because of glycolysis, that is, consumption of the sugar component by the cells in the blood. Therefore, an additive or reagent for inhibiting glycolysis in blood that is collected and stored for a period of time prior to testing is needed.

A typical antiglycolytic agent, sodium fluoride has been used to reduce glycolysis in blood. Sodium fluoride is associated with antiglycolytic action as well as hemolytic toxicity and anticoagulant activity.

However, the anticoagulant activity of the sodium fluoride is not sufficient at the low additive levels required for antiglycolytic action and averting hemolysis. Therefore the blood sample treated with sodium fluoride only is not suitable for the analysis of the sugar content by methods affected by hemolysis in the plasma. Therefore, sodium fluoride used as an anticoagulant agent limits the subsequent method of blood sugar analysis. To remedy the shortcoming of sodium fluoride, another component could be combined with the sodium fluoride so as to form an additive formulation for use in blood collection devices. A low hemolytic toxicity type of component is desirable for the anticoagulant, since hemolysis in the specimen will affect the glucose values.

Freeze drying, vacuum drying, liquid filing and powder filling are the conventional methods for filling additive formulations into blood collection devices. However, these conventional methods have disadvantages. In the case of freeze-drying, additive formulations can be rehydrated again after drying, which is not desirable. With drying methods, the additive formulations tend to be localized within the tube. Also, vacuum drying process may adversely affect the dissolution characteristics of the additives.

Powder filling of formulations is currently used to produce additives, that have more than two (2) components, wherein the components are dry blended before filling into the tube. However, it is very difficult to blend and fill because the component ratios vary due to the different specific gravity and particle size of each component. Powder mixing consists of siffting the components and then mixing in a high speed mixer. The result is a bulk powder mixture that is then dispensed into a tube. Each component separates from the other in the dry blended powder formulation by shock or vibration. As a result, the component ratio varies in each tube.

Liquid filling is not practical because of the low solubility of the antiglycolytic and anticoagulant components of the additives. Due to the low solubility, large liquid fills are required which reduce the glucose value of the resulting plasma sample by dilution. In addition, liquid filling is not practical because liquid additives are subject to permeation through plastic tubes which will lead to drying of the additive and poor dissolution characteristics.

A need has therefore been identified for solid additive formulations with improved fill and reduced hemolysis properties for blood collection devices. Blood collection tubes need to be designed in such a manner that additive fill formulations in tubes efficiently work in tests or analysis, and the formulations do not interfere with testing or analysis. Such tests include but are not limited to hematology, blood chemistry, blood typing, toxicology analysis and therapeutic drug monitoring.

SUMMARY OF THE INVENTION

The present invention is a blood collection device with an additive formulation comprising a low solubility component, fluoride salt and a high solubility component, an anticoagulant, wherein the additive particle formulation has a mesh size of about 130 to about 350.

Preferably, the fluoride salt is sodium fluoride, lithium fluoride, potassium fluoride or ammonium fluoride.

Preferably, the anticoagulant is ethylenediaminetetraacetate salt (EDTA) or a heparin salt. The heparin salt may be sodium heparin, lithium heparin or ammonium heparin.

Preferably, the EDTA salt may be ethylenediaminetetraacetate disodium (EDTA-2Na) or ethylenediaminetetraacetate dipotassium (EDTA-2K).

Preferably, the additive particle formulation comprises about 1.0 mg to about 10.0 mg of fluoride salt and about 1.0 mg to about 10.0 mg of EDTA or about 1.0 United States Pharmacopeia (USP) unit to about 20.0 USP units of heparin salt per 1.0 ml of blood and most preferably about 1.5 mg of fluoride salt and about 3.0 mg of an EDTA or 10 USP units of heparin salts per 1.0 ml of blood.

The additive particle of the present invention is formulated by a method comprising the following steps:

(a) mixing a fluoride salt and an anticoagulant; (b) adding distilled water to the mixture; (c) forming the mixture into particles; (d) heat-drying the particles until the moisture content of the particles is less than about 0.5% excluding water of crystallization; (e) milling the particles; and (f) sieving the particles to obtain particles having a mesh size of about 130 to about 350.

Most preferably, the mesh size of the additive particles is about 130 to about 180.

The forming step is preferably spraying-dying, extruding, granulating and the like.

The form and grain size of the additive particles are uniform and therefore its disintegration and dissolution velocity also uniform. Therefore, the effects of the additive on the blood, namely its capacity to prevent glycolysis and coagulation are constant. It is believed that as the high solubility component of the particle dissolves, it disperses the lower solubility component, in this case the fluoride salt, into the blood specimen increasing its surface area available for dissolution.

With this invention, in contrast to the commercially available additives in tubes, the additive particle formulation of the present invention comprising a fluoride salt and an anticoagulant, having a mesh size of about 130 to 350, can be more easily filled into a blood collection tube. A blood collection tube with this particle formulation will provide the desired antiglycolysis and anticoagulation properties to the specimen collected with low hemolysis.

Furthermore, the additive particle formulation of the present invention provides more consistent results as compared to the commercially available additive formulations. Commercially available additive formulations consist of blended powder formulations comprising sodium fluoride and EDTA. In the blended powder mixtures, the density and particle size of each component varies, causing the ratios to change during tube filing process.

Such commercially available products include VACUTAINER® Glass Tubes containing a powder fill of sodium fluoride and ethylenediaminetetraacetate disodium, Order No. 367728 (Becton, Dickinson and Company, 1 Becton Drive, Franklin Lakes, N.J. 07417-1880).

The additive particle formulations of the present invention provides better and more consistent contact with the blood specimen and therefore more rapid dissolution of the additive particle into the blood specimen is facilitated, and the initiation of glycolysis and coagulation of the blood specimen is prevented.

Most notably, the additive particle formulation of the present invention provides a more stable blood to additive concentration over the shelf life of the device so that the product performance over the shelf-life of the product remains more consistent.

Additionally, the additive particle formulation of the present invention has substantially improved flow characteristics as compared to a powder blended formulations of the same components.

Unlike the conventional fill processes, the additive particle of the present invention does not require preparing solution, mixing powder or a drying procedure after filing additive. Preparation and validation of a powder blended formulation is time consuming and does not provide consistent formulation. Furthermore, there is a substantial material waste and homogeneity of the powder blend is difficult to maintain. In addition, the dispensing process of milligram quantities of powder blend may result in individual tube aliquots which may differ substantially from the needed blend ratio. Thus preparation and control of a granulated additive particle formulation is simple and efficient and provides a more accurate and reliable means for inhibiting coagulation and glycolysis in a sample.

Furthermore, there is a cost advantage with the device and the method for making the same according to the present invention. The increased precision in providing a granulated particle additive formulation into the tube enables lower amounts of components to be used. Therefore, waste during manufacturing is minimized and cost reductions are realized.

The additive particle formulation improves collection and analysis of blood by a number a factors: (i) a direct sampling device nozzle or probe of an automatic analyzer is less likely to clog because the formation of fibrin in the plasma is reduced due to the improved anticoagulation of the sample; (ii) improved additive fill due to the consistency of the components in the fill; and (iii) improved dissolution rate of the low solubility component due to dispersion of the low solubility component, within the high solubility component.

Thus the method and additive particle formulation of the present invention imparts to the collection devices and the samples contained therein, combined anticoagulation and antiglycolysis properties.

The additive particle formulation of the present invention has improved additive fill due to the consistency of the components of the particle. The variation in fill of the fluoride salt and the anticoagulant is reduced since error is then limited to fill error and not the combination of fill error and segregation error. Segregation error is caused due to separation of chemical components on account of their density and particle size differences during process of filling. Additionally, the volumetric fill error itself is reduced by controlling the particle size range. Furthermore, reducing the overall variation in fill quantities of the subcomponents improves specimen quality by maintaining optimal additive to blood ratios. Therefore, the performance of the additive particle formulation is reliable and consistent.

The additive particle formulation of the present invention has the further advantage over conventional additive formulations in that hemolysis is minimized in a blood sample with use of the granulated particle additive, and therefore no false data of the blood glucose value. Because of the multiplicity of instrumentation and variations in methods for the measurement of glucose, the magnitude of the effect of hemolysis on each glucose procedure is important. As such for accurate glucose measurements, it is therefore desirable to avoid or minimize hemolysis by using the granulated additive particle of the present invention. Furthermore, typical additive formulations cause hemolysis with passage of time after blood collection, and therefore the specimen is most likely to exhibit false data of the glucose value by the colorimetric assay method.

DETAILED DESCRIPTION

Figure 1:
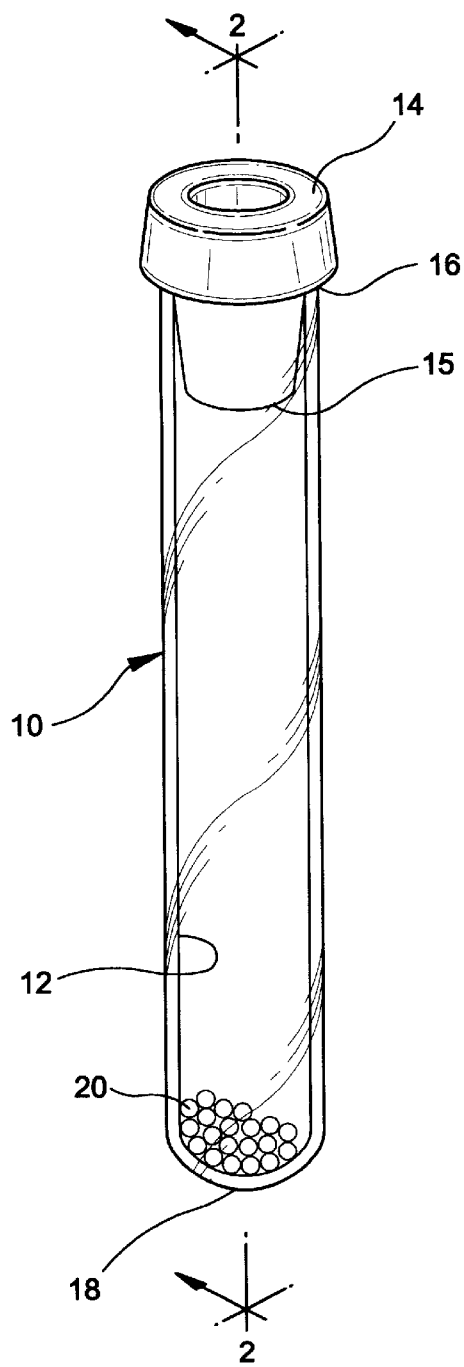
FIG. 1 is a perspective view of a typical blood collection tube with a stopper.

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The additive particle formulation of the present invention preferably comprises a low solubility component and a high solubility component. Combining the additive components together increases the dissolution rate of the low solubility component, due to the dispersion of the low solubility component, within the high solubility component. Therefore, the surface area of the low solubility component is exposed as the high solubility component dissolves in the blood specimen. Most preferably, the low solubility component is a fluoride salt and the high solubility component is an anticoagulant.

Preferably, the fluoride salt is sodium fluoride, lithium fluoride, potassium fluoride or ammonium fluoride. Most preferably, the fluoride salt is sodium fluoride.

Preferably, the anticoagulant is ethylenediaminetetraacetate salt (EDTA) or a heparin salt. The heparin salt may be sodium heparin, lithium heparin or ammonium heparin.

Preferably, the EDTA salt may be ethylenediaminetetraacetate dissodium (EDTA-2$N_a$) or ethylenediaminetetraacetate dipotassium (EDTA-2K).

Preferably, the additive particle formulation, per 1 ml of blood, comprises:

(a) from about 1.0 to about 10.0 mgs of a fluoride salt; and (b) from about 1.0 to about 10.0 mgs of an EDTA salt or from about 1.0 USP unit to about 20 USP units of a heparin salt.

Most preferably, the additive particle formulation comprises, per 1 ml of blood, about 1.5 mg of a fluoride salt and about 3.0 mg of an EDTA salt or 10 USP units of a heparin salt.

Preferably the particle mesh size of the additive formulation is about 130 to about 350 and most preferably from about 130 to about 180.

The additive particle formulation is prepared by a method comprising the following steps: (a) mixing sodium fluoride and an EDTA salt or a heparin salt; (b) adding distilled water to the mixture; (c) forming the mixture into particles; (d) heat-drying the particles until the moisture content of the particles is less than about 0.5% excluding water of crystallization; (e) milling the particles; and (f) sieving the particles to obtain granulated particles having a mesh size of about 130 to about 350.

Preferably the forming step is spraying-drying, extruding, granulating and the like.

Combining the additive components together increases the dissolution rate of the low solubility components (fluoride salt) due to the dispersion of the low solubility component within the high solubility component (anticoagulant). Therefore, the surface area of the low solubility component is exposed and increases as the high solubility component dissolves.

The advantages of a tube with the additive particle formulation of the present invention is more precise and uniform fill, stable test values, lower hemolysis and good dissolution rate of the particle into a blood specimen. Furthermore, the exposure of the particle to a blood specimen is enhanced.

A blood collection device of the present invention can be either an evacuated blood collection device or a non-evacuated blood collection device. The blood collection device is desirably made of polyethylene terephtahlate or polypropylene.

Water is most preferably used as the solvent for mixing and forming the particle because water has minimal detrimental effects on product or environment.

A variety of other compounds can be formed into the particles. Such things include, but are not limited to, polyvinypyrrolidone and carboxymethylcellulose.

Referring to the drawings in which like parts throughout the several views thereof, FIG. 1 shows a typical blood collection tube 10, having an open end 16, a closed end 18, and a stopper 14 that includes a lower annular portion or skirt 15 which extends into and processes against the inside wall 12 of the tube for maintaining stopper 14 in place.

Figure 2:
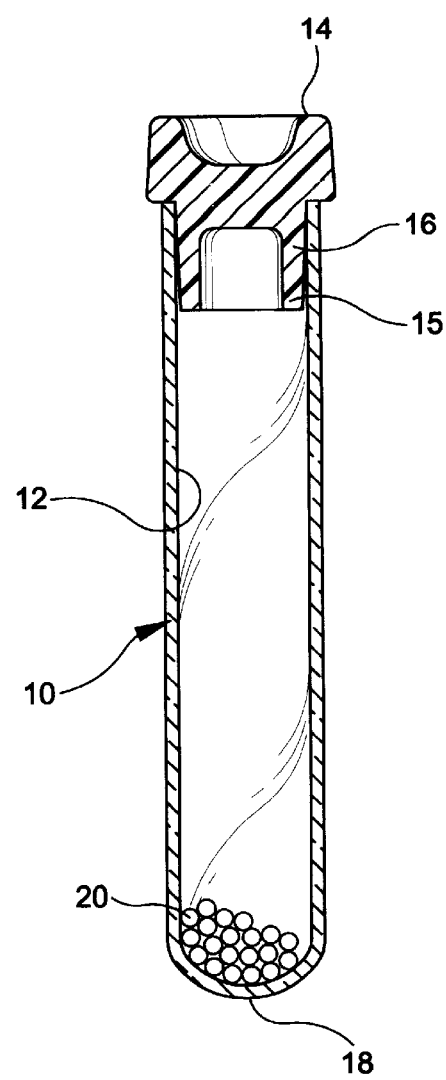
FIG. 2 is a longitudinal sectional view of the tube of FIG. 1 taken along line 2—2, comprising the particle additive formulation of the present invention.

FIG. 2 shows the particle of the formulation of the present invention in a typical blood collection tube. The particle additive formulation 20 is shown near the closed end of the tube.

A blood sample of interest can be transferred into tube 10 that comprises particle additive formulation 20. The blood sample efficiently contacts particle additive formulation 20 so that particle additive formulation 20 rapidly dissolves into the blood sample and glycolysis and blood coagulation is substantially prevented for a period of time.

Various other modifications will be apparent to and may be readily made by those skilled in the art without departing from the scope and spirit of the invention.

The examples are not limited to any specific embodiment of the invention but are only exemplary.

EXAMPLE 1

PREPARATION OF ADDITIVE PARTICLE FORMULATION

A particle formulation was prepared by dissolving about 50 g of sodium fluoride and about 100 g of EDTA-2Na in about 30 mls of distilled water. The aqueous formulation was then formed and dried into particles. The particles were then milled and sieved to a mesh size of about 130 to 180. In each tube, 9 mgs of the formulation was placed.

The tubes were each evacuated for drawing 2 ml of blood and sealed with a closure and sterilized by gamma irradiation at 2.5 mega Rads.

EXAMPLE 2

COMPARATIVE ANALYSIS OF THE PERFORMANCE OF ADDITIVE PARTICLE FORMULATION TO COMMERCIALLY AVAILABLE ADDITIVE FORMULATIONS

The additive particle formulation prepared in Example 1 was examined in 13×100 mm size evacuated blood collection tubes (in both glass and plastic) with 2 mL draw. A 9 mg quantity of nominal particles were filled into each type of tube. The control used was VACUTAINER® Brand evacuated tube (glass, 13×100 mm, 7.0 mL). 24.5 mg nominal additive amount powder mixture of sodium fluoride and disodium EDTA was filled into each control tube.

Twenty (20) donors provided blood specimens wherein each donor provided a blood specimen into three (3) VACUTAINER® tubes containing blended powder additive, three (3) plastic tubes containing additive particle formulation and three (3) glass tubes with additive particle formulation. Therefore, sixty (60) VACUTAINER® tubes containing blended powder additive, sixy (60) plastic tubes containing additive particle (PLASTIC) and sixty (60) glass tubes containing additive particles, (GLASS) were examined.

Immediately after draw, the tubes were mixed using 10 complete inversions. The tubes were then stored. After 4 hours of storage, 20 tubes of each type were centrituged at 1,000 RCF for 10 (±2) minutes at 25° C. The plasma from each specimen was visually assessed for hemolysis and then analyzed for glucose on the Roche COBAS FARA® II (a trademark of Roche Diagnostics, Branchburg, N.J.) using the Hexokinase method. The specimens of the tubes were then remixed and poured through an ASTM #50 wire mesh sieve (sold by Fischer Scientific, Inc., Orangeburg, N.Y.) to check for blood clots. After 72 hours of storage, 20 tubes of each type (control, plastic and glass) were tested as described above. Evaluation of the plasma for visual hemolysis only was made on all the tubes at both 24 and 48 hours after collection.

Clinical testing indicated no incidence of visual hemolysis in the tubes containing the particle additive formulation even after 72 hours (at room temperature as well as 4° C.). This is also indicated by lower increase in glucose values for evaluation tubes than the control tube. The data also indicates a smaller increase in the glucose values over the 72 hour period than the control product, indicating better stability of the tubes containing the additive particle formulation. Table 1 summarizes the results of the clinical tests.

In conclusion the additive particle formulation shows an improved performance in hemolysis and clotting over powder blended additive formulation. Also the additive particle formulation is more resistant to increase the glucose values of the sample over time, indicating better specimen stability.

Since all evaluation tubes indicated higher initial glucose values than the control, it can be inferred that the plastic and glass tubes containing additive particles dissolves faster and hence glycolysis inhibition is better than using a glass tube with a blended powder additive formulation.

TABLE 1

Clinical Test Data on Commercially Available Product v/s Prototyped
(R.T. is Room Temperature, Glucose Measurement Method: Hexokinase)

| Tube Type | Hemolysis (Number of Tubes Indicating Hemolysis) | | | | | Clotting (Number of Tubes Indicating Clotting) | | | Glucose Value | | |
|---|---|---|---|---|---|---|---|---|---|---|---|
| | 4 hr | 24 hr | 48 hr | 72 hr (4° C.) | 72 hr (R.T) | 4 hr | 72 hr (4° C.) | 72 hr (R.T) | 4 hr. (Pop. means in mg/dL) | 72 hr (4° C.) Pop. means in mg/dL) | 72 hr (RT) (Pop. means in mg/dL) |
| Control | 0 | 0 | 0 | 12 | 10 | 2 | 2 | 2 | 92.8 | 93.9 | 101.1 |
| Plastic Evaluation | 0 | 0 | 0 | 0 | 0 | 0 | 0 | 0 | 94.3 | 94.9 | 98.6 |
| Glass Evaluation | 0 | 0 | 0 | 0 | 0 | 0 | 0 | 0 | 96.9 | 94.3 | 96.7 |

What is claimed is:

1. An article of manufacturing comprising, a blood collection tube containing granulated additive particles wherein each particle comprises a fluoride salt component and an anticoagulant component wherein said particles have a mesh size from 130 to 350.

2. The article of claim 1 wherein the mesh size of said particles are from 130 to 180.

3. The article of claim 1 wherein said fluoride salt is selected from the group consisting of sodium fluoride, lithium fluoride, potassium fluoride and ammonium fluoride.

4. The article of claim 3 wherein said fluoride salt is sodium fluoride.

5. The article of claim 1, wherein said blood collection device is plastic.

6. The article of claim 1 wherein said anticoagulant is selected from the group consisting of an ethylenediaminetetraacetate salt and a heparin salt.

7. The article of claim 6 wherein said ethylenediaminetetraacetate salt is selected from the group consisting of ethylenediaminetetraacetate disodium and ethylenediaminetetraacetate dipotassium.

8. The article of claim 6 wherein said heparin salt is selected from the group consisting of sodium heparin, lithium heparin and ammonium heparin.

9. The article of claim 6, wherein said additive particle, per 1 ml of blood, comprises:
   (a) about 1.0 mgs to about 10.0 mgs of a fluoride salt; and
   (b) about 1.0 mgs to about 10.0 mgs of an ethylenediaminetetraacetate salt or about 1.0 USP to about 20.0 USP of a heparin salt.

10. The article of claim 6 wherein said additive particle, per 1 ml of blood, comprises about 1.5 mg of a fluoride salt component and about 3.0 mg of an ethylenediaminetetraacetate salt.

11. A granulated additive particle formulation for use in blood collection tubes to minimize glycolysis and blood coagulation with low hemolysis, comprising a fluoride salt component and an anticoagulant component, wherein each particle has a mesh size from 130 to 350.

12. The additive of claim 11 wherein the mesh size of said particle is from 130 to 180.

13. The additive of claim 11 wherein said fluoride salt is selected from the group consisting of sodium fluoride, lithium fluoride, potassium fluoride and ammonium fluoride.

14. The additive of claim 13 wherein said fluoride salt is sodium fluoride.

15. The additive of claim 13 wherein said anticoagulant is selected from the group consisting of an ethylenediaminetetraacetate salt and a heparin salt.

16. The additive of claim 15 wherein said ethylenediaminetetraacetate salt is selected from the group consisting of ethylenediaminetetraacetate disodium and ethylenediaminetetraacetate dipotassium.

17. The additive of claim 15 wherein said heparin salt is selected from the group consisting of sodium heparin, lithium heparin and ammonium heparin.

18. The additive of claim 15 per 1 ml of blood, comprising:
   (a) 1.0 mg to 10.0 mg of a fluoride salt; and
   (b) 1.0 mg to 10.0 mg of an ethylenediaminetetraacetate salt or 1.0 USP to 20.0 USP of a heparin salt.

* * * * *